United States Patent
Sun et al.

(10) Patent No.: US 8,358,822 B2
(45) Date of Patent: Jan. 22, 2013

(54) AUTOMATIC DETERMINATION OF FIELD OF VIEW IN CARDIAC MRI

(75) Inventors: Ying Sun, Singapore (SG); Jens Gühring, Monmouth Junction, NJ (US); Peter Speier, Erlangen (DE); Michaela Schmidt, Uttenreuth (DE); Jordin D. Green, Calgary (CA); Christine H. Lorenz, Frederick, MD (US); Marie-Pierre Jolly, Hillsborough, NJ (US)

(73) Assignee: Siemens Aktiengesellschaft, Munich (DE)

( * ) Notice: Subject to any disclaimer, the term of this patent is extended or adjusted under 35 U.S.C. 154(b) by 609 days.

(21) Appl. No.: 12/393,236

(22) Filed: Feb. 26, 2009

(65) Prior Publication Data

US 2009/0290776 A1 Nov. 26, 2009

Related U.S. Application Data

(60) Provisional application No. 61/055,174, filed on May 22, 2008.

(51) Int. Cl.
*G06K 9/00* (2006.01)
(52) U.S. Cl. ...................................................... 382/128
(58) Field of Classification Search .................. 382/128, 382/130–132
See application file for complete search history.

(56) References Cited

U.S. PATENT DOCUMENTS

| 7,958,100 B2 * | 6/2011 | Judd et al. .................... 707/705 |
| 2007/0036419 A1 * | 2/2007 | Jabri et al. .................... 382/132 |

* cited by examiner

*Primary Examiner* — Hwa Lee

(57) ABSTRACT

A method for automatically determining a field of view for performing a subsequent medical imaging study includes acquiring one or more preliminary images. A body mask is generated by thresholding the preliminary images and identifying a largest connected component. A boundary mask is obtained from the boundary of the generated body mask. A rectangular bounding box is fit to the obtained boundary mask. The rectangular bounding box is used as a field of view for performing a subsequent medical imaging study.

15 Claims, 7 Drawing Sheets

AUTOMATIC DETERMINATION OF FIELD OF VIEW IN CARDIAC MRI

CROSS-REFERENCE TO RELATED APPLICATION

The present application is based on provisional application Ser. No. 61/055,174, filed May 22, 2008, the entire contents of which are herein incorporated by reference.

BACKGROUND OF THE INVENTION

1. Technical Field

The present disclosure relates to cardiac MRI and, more specifically, to the automatic determination of a field of view in cardiac MRI.

2. Discussion of Related Art

Magnetic resonance imaging (MRI) is a medical imaging technique in which a human subject can be imaged in three-dimensions with a great deal of detail pertaining to the differentiation of different forms of bodily soft tissue. Thus MRI is well suited for the visualization and diagnosis of cardiovascular disease. In MRI, the human subject is exposed to a powerful magnetic field which aligns the nuclear magnetization of hydrogen atoms in water within bodily tissues. Radiofrequency fields are used to systematically alter the alignment of this magnetization and the hydrogen nuclei then produce a rotating magnetic field detectable by the scanner.

Structural image data may be generated from the received data signals to construct an image of the body. For example, the structural image may be generated from a number of spatial frequencies at different orientations. Frequency and phase encoding are used to measure the amplitudes of a range of spatial frequencies within the object being imaged. The number of phase-encoding steps performed may be selected to determine how much imaging data may be collected.

As MRI uses magnetic and radiofrequency fields to perform visualization, the patient is not exposed to potentially hazardous ionizing radiation as would be the case with CT scans.

In MRI, spatial resolution may generally be determined by the size of the field of view (FOV) and the number of phase-encoding steps performed during scanning. Thus, to achieve a greater spatial resolution and a higher level of image detail, the FOV may be reduced and/or the number of phase-encoding steps may be increased. For a given number of phase-encoding steps, a smaller FOV will result in a higher resolution MR image.

However, MR images may be prone to wrap-around artifacts in which a part of the imaged anatomy from the periphery of the FOV appears on an opposite side of the periphery of the FOV, with respect to the phase encoding direction, as if structures that should be on one side of the image appear on an opposite side of the image. Wrap-around artifacts may occur, for example, when the boundary of the FOV intersects with the subject's body. If the FOV is too small, the wrap-around region may intersect anatomy displayed on the opposite side of the image.

FIG. 6 is a set of four MR images (a), (b), (c), and (d) illustrating wrap-around artifacts. The four images show distinct MR views, however, in image (b), it can be seen that the right margin of the image 61 has been cut off and appears as wrap-around artifact 62 on the left margin. Similarly, in image (d), it can be seen that the bottom margin of the image 63 has been cut off and appears as a wrap-around artifact 64 on the top margin.

Wrap-around artifacts are not a problem for MR imaging so long as the region of the body that is the focus of the MR study is sufficiently far from the periphery of the FOV so that any wrap-around artifacts do not obstruct the region of the body that is the focus of the MR study. Accordingly, it is important that the FOV not be set too small or there will be an increased possibility that wrap-around artifacts will interfere with the diagnostic value of the study.

Accordingly, an optimal FOV may be selected such that the size of the FOV is small enough to produce a sufficiently high resolution image, and yet large enough in the phase encoding direction to prevent the occurrence of wrap-around artifacts from obstructing the region of the body that is the focus of the MR study, which may be, for example, the heart.

The FOV is accordingly manually selected by a trained medical practitioner or technician to achieve the desired results. However, this manual selection may be time consuming and prone to human error.

SUMMARY

A method for automatically determining a field of view for performing a subsequent medical imaging study includes acquiring one or more preliminary images. A body mask is generated by thresholding the preliminary images and identifying a largest connected component. A boundary mask is obtained from the boundary of the generated body mask. A rectangular bounding box is fit to the obtained boundary mask. The rectangular bounding box is used as a field of view for performing a subsequent medical imaging study.

The acquired preliminary images may be preprocessed prior to the generation of the body mask. Preprocessing the preliminary images may include removing blank preliminary images, cropping regions without image data from the periphery of the preliminary images, establishing an initial field of view for each of the preliminary images, removing preliminary images where the initial field of view is not sufficiently large, correcting for shift artifacts, and correcting for in homogeneity.

The one or more preliminary images may be one or more two-dimensional localizer images of a lower diagnostic value than the subsequent medical imaging study.

Thresholding the preliminary images may include applying an adaptive thresholding technique to the preliminary images to characterize each image pixel as either a one, where the pixel intensity is above the adaptive threshold, or a zero, where the pixel intensity is below the adaptive threshold. The largest connected component may be identified as the single region of the preliminary image that has the highest number of contiguous pixels with a value of one.

Obtaining the boundary mask may include defining a first boundary mask as the boundary of the body mask, refining the body mask to establish a refined body mask, defining a second boundary mask as the boundary of the refined body mask, and creating the final boundary mask as the intersection of the first boundary mask and the second boundary mask, wherein the obtained boundary mask is the final boundary mask.

Fitting the rectangular bounding box to the obtained boundary mask may include fitting an ellipse to the obtained boundary mask, refining the fitted ellipse, and setting the bounding box as the smallest possible rectangle that can enclose the fitted ellipse.

The medical imaging study may be an MRI.

The method may further include detecting and correcting for wrap-around in the one or more preliminary images after generating the body mask and prior to obtaining the boundary mask.

The boundary mask may include not only the largest connected component of the body mask but also structures proximate to the largest connected component.

A system for automatically determining a field of view for performing a subsequent medical imaging study includes a medical imaging device for acquiring one or more two-dimensional localizer images and a three-dimensional subsequent medical imaging study, a body mask generation unit for thresholding the localizer images and identifying a largest connected component, a boundary mask obtaining unit for obtaining a boundary mask from the boundary of the generated body mask, and a field of view determining unit for fitting a rectangular bounding box to the obtained boundary mask. The determined file of view is used by the medical imaging device in performing the subsequent medical image study.

The system may additionally include a preprocessing unit for preprocessing the acquired localizer images prior to generating the body mask.

The preprocessing unit may be adapted for removing blank localizer images, cropping regions without image data from the periphery of the localizer images, establishing an initial field of view for each of the localizer images, removing localizer images where the initial field of view is not sufficiently large, correcting for shift artifacts, and correcting for inhomogeneity.

The boundary mask obtaining unit may be adapted for defining a first boundary mask as the boundary of the body mask, refining the body mask to establish a refined body mask, defining a second boundary mask as the boundary of the refined body mask, and creating the final boundary mask as the intersection of the first boundary mask and the second boundary mask. The obtained boundary mask may be the final boundary mask.

The system may further include a wrap-around correcting device for detecting and correcting for wrap-around in the one or more localizer images.

A computer system includes a processor and a program storage device readable by the computer system, embodying a program of instructions executable by the processor to perform method steps for automatically determining a field of view for performing a subsequent medical imaging study. The method includes acquiring one or more two-dimensional localizer images. The localizer images are preprocessed. A body mask is generated by thresholding the preprocessed localizer images and identifying a largest connected component. A boundary mask is obtained from the boundary of the generated body mask. A rectangular bounding box is fit to the obtained boundary mask. The rectangular bounding box is used as a field of view for performing a three-dimensional subsequent medical imaging study.

Preprocessing the localizer images may include removing blank localizer images, cropping regions without image data from the periphery of the localizer images, establishing an initial field of view for each of the localizer images, removing localizer images where the initial field of view is not sufficiently large, correcting for shift artifacts, and correcting for inhomogeneity.

Thresholding the localizer images may include applying an adaptive thresholding technique to the localizer images to characterize each image pixel as either a one, where the pixel intensity is above the adaptive threshold, or a zero, where the pixel intensity is below the adaptive threshold. The largest connected component may be identified as the single region of the localizer image that has the highest number of contiguous pixels with a value of one.

Obtaining the boundary mask may include defining a first boundary mask as the boundary of the body mask, refining the body mask to establish a refined body mask, defining a second boundary mask as the boundary of the refined body mask, and creating the final boundary mask as the intersection of the first boundary mask and the second boundary mask. The obtained boundary mask may be the final boundary mask.

The computer system may further include detecting and correcting for wrap-around in the one or more localizer images after generating the body mask and prior to obtaining the boundary mask.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings, wherein.

DETAILED DESCRIPTION OF THE DRAWINGS

Figure 1:
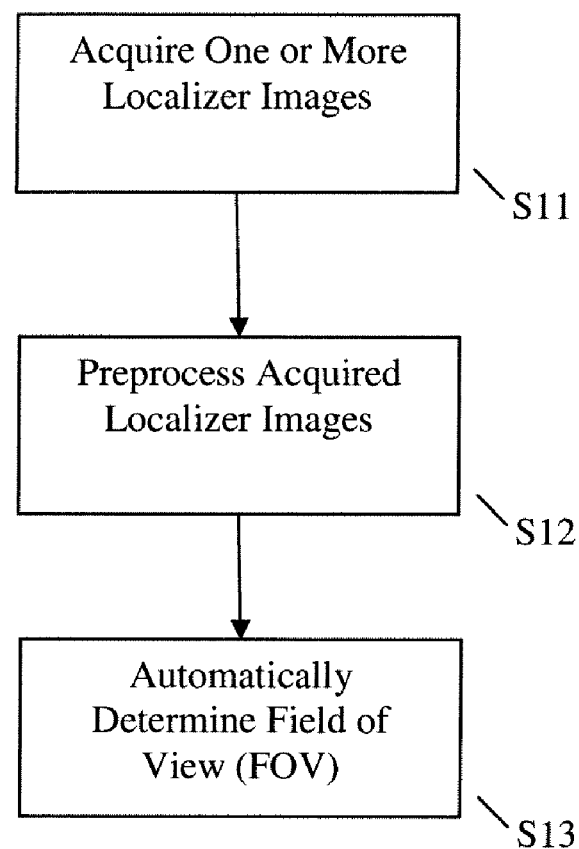
FIG. 1 is a flow chart illustrating an overview approach for automatically determining a field of view (FOV) for a cardiac MRI according to an exemplary embodiment of the present invention.

In describing exemplary embodiments of the present disclosure illustrated in the drawings, specific terminology is employed for sake of clarity. However, the present disclosure is not intended to be limited to the specific terminology so selected, and it is to be understood that each specific element includes all technical equivalents which operate in a similar manner.

Exemplary embodiments of the present invention seek to provide approaches for automatically determining a field of view (FOV) for magnetic resonance images (MRIs), and in particular, to automatically determine a FOV for cardiac MRI. FOVs so determined may minimize FOV size while preventing the occurrence of wrap-around artifacts from obstructing the region of the body that is the focus of the MR study, which may be, for example, the heart. By providing an automatic determination, FOV selection may be fast, accurate, free from human error, and may produce more consistency than FOVs that are manually determined.

In cardiac MRI, multiple localizer images are generally obtained prior to performing the MRI study. The localizer images may be two-dimensional scans that are of a relatively low resolution and may be obtained quickly. Multiple localizer images may be obtained in several imaging planes that are parallel and perpendicular to the cardiac axes. Exemplary embodiments of the present invention seek to utilize the localizer images to perform automatic FOV determination. By providing an automated determination of the FOV, exemplary embodiments of the present invention may be combined with other MRI automation techniques to provide a fully automated workflow for cardiac MRI.

Exemplary embodiments of the present invention may include three general steps, as seen, for example, in FIG. 1. In the first step, one or more localizer images are acquired (Step S11). As discussed above, the acquisition of the localizer images may include performing a series of quick two-dimensional scans to visualize the heart from multiple planes that are parallel and/or perpendicular to the cardiac axes. These quick scans may be performed at a resolution that is below that of diagnostic quality.

In the next step, the acquired localizer images may be preprocessed (Step S12). Preprocessing of the localizer images may include one or more steps that seek to optimize the localizer images for efficient automatic selection of the FOV. The need for preprocessing may vary depending upon the requirements of the particular FOV determination problem. Similarly, the steps taken in performing preprocessing may vary. In this respect, preprocessing is an optional step and may be omitted, where unnecessary. An example of a preprocessing technique according to an exemplary embodiment of the present invention is described in detail below with reference to FIG. 2.

In the final step, the FOV may be automatically determined base on the preprocessed acquired localizer images (Step S13). Automatic FOV determination may be performed using one or more approaches of the present disclosure. Examples of automatic FOV determination techniques according to exemplary embodiments of the present invention are described in detail below with respect to FIGS. 3 and 4.

Figure 2:
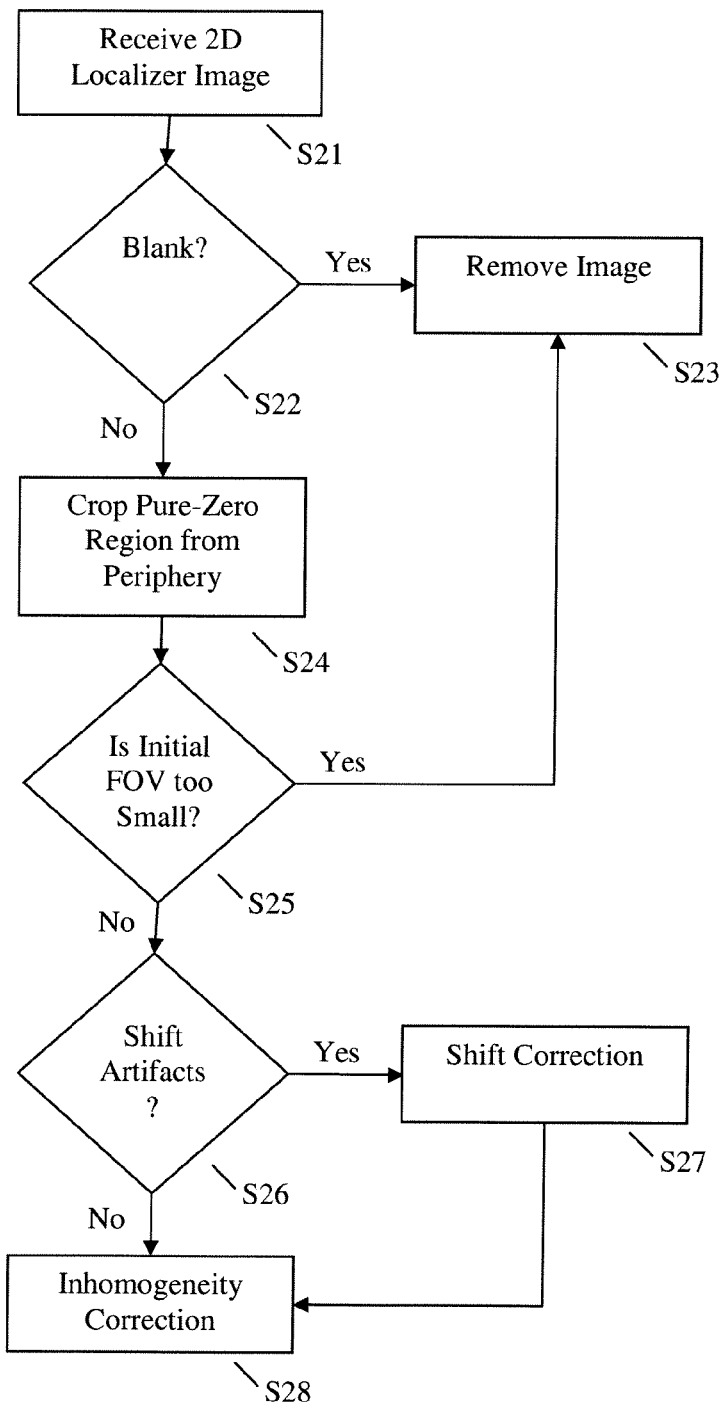
FIG. 2 is a flow chart illustrating an approach for preprocessing one or more localizer images for the subsequent performance of automatic FOV determination according to an exemplary embodiment of the present invention.

FIG. 2 is a flow chart illustrating an approach for preprocessing one or more localizer images for the subsequent performance of automatic FOV determination according to an exemplary embodiment of the present invention. The goal of the preprocessing stage may be to check each localizer image to ensure that it is significant and then condition each image to facilitate automatic FOV determination. Preprocessing may have the following steps: First, a two-dimensional localizer image may be received (Step S21). Next, it may be determined whether the received localizer image is blank (Step S22). As each localizer image is a two-dimensional scan along a particular plane, it is possible that one or more localizer images will not include any structural details. For example, when the localizer image includes a plane that is above the top surface of the patient, or past the head, feet or arms of the patient, the localizer image may be blank. Multiple blank localizer images may be seen, for example, when the patient is of a small size, for example, when the patient is a child. As such localizer images may not be useful in establishing a FOV, it may be preferable to remove blank localizer images to reduce processing time. Accordingly, when it is determined that the received localizer image is blank (Yes, Step S22), the blank localizer image may be removed from consideration (Step S23).

When, however, it is determined that the localizer image is not blank (No, Step S22), the non-blank localizer image may be cropped to remove regions of the image from the periphery that include no image data (pure-zero regions) (Step S24). In so doing, the localizer image may be reduced in size to the exclusion of regions of the outer periphery that would play no role in determining the FOV. These regions of no image data are described as "pure-zero" regions because it includes a grouping of pixels with an intensity value of essentially zero. However, it is certainly possible that these pure-zero regions will include some pixels with a non-zero intensity value, as there may be a degree of noise in the image that results in pixel intensity. These regions of noise may still be cropped out from the localizer image. The cropping may be limited to pure-zero regions that occur at the periphery of the localizer image. Regions of pure-zero intensity values that are well within the boundaries of the localizer image need not be removed from the localizer image. Moreover, cropping may be performed while maintaining a rectangular shape of the localizer image such that the top, bottom, and sides of the localizer image all remain as straight lines with perpendicular corners. This is to say, the resulting cropped localizer image should have a rectangular shape.

After the localizer image has been cropped (Step S24), an initial FOV may be established and it may be determined whether the initial FOV is too small (Step S25). The initial FOV may be set as, for example, a maximum field of view or alternatively, some other approach may be used. However, if the initial FOV is determined to be too small (Yes, Step S25) then the localizer image may be removed from consideration (Step S23). It may be determined that the initial FOV is too small, if for example, the periphery of the localizer image contains substantial image data.

If it is determined that the initial FOV is no too small (No, Step S25), then it may be determined whether there are shift artifacts present in the localizer image (Step S26). Shift artifacts are image artifacts that result from wrap-around artifacts in the preliminary images themselves. Shift artifacts may result in spatial inconsistencies of particular pixels which may be displaced in the direction of frequency encoding.

While it may be possible to simply discard preliminary images that show signs of shift artifacts, it may be preferable to correct for wrap-around in the preliminary images so that the affected preliminary images may still be used in automatically determining the final FOV.

As shift artifacts present in the localizer image may interfere with the accurate automatic determination of the FOV, exemplary embodiments of the present invention correct for the shift artifacts caused by wrap-around by applying shift correction (Step S27) when it is determined that shift artifacts are present in the localizer image (Yes, Step S26). When, however, it is determined that there are no shift artifacts present in the localizer image (No, Step S26), or after shift correction has been performed (Step S27), inhomogeneity correction may then be applied (Step S29).

Inhomogeneity generally refers to the effects of unevenness in the magnetic field being applied during image acquisition. This unevenness may result in portions of the localizer image showing lighter and darker pixel intensities than would be expected if the magnetic field were completely uniform. As inhomogeneity may also interfere with the automatic determination of the FOV, exemplary embodiments of the present invention may provide for inhomogeneity correction (Step S29).

Preprocessing may include one or more additional steps and/or one or more steps listed above may be omitted. Preprocessing may be performed on one or more of the localizer images that are acquired. It may also be the case that preprocessing is omitted in its entirety from the practice of exemplary embodiments of the present invention. However, when preprocessing is performed, automatic FOV determination may be performed on the preprocessed localizer images.

Figure 3:
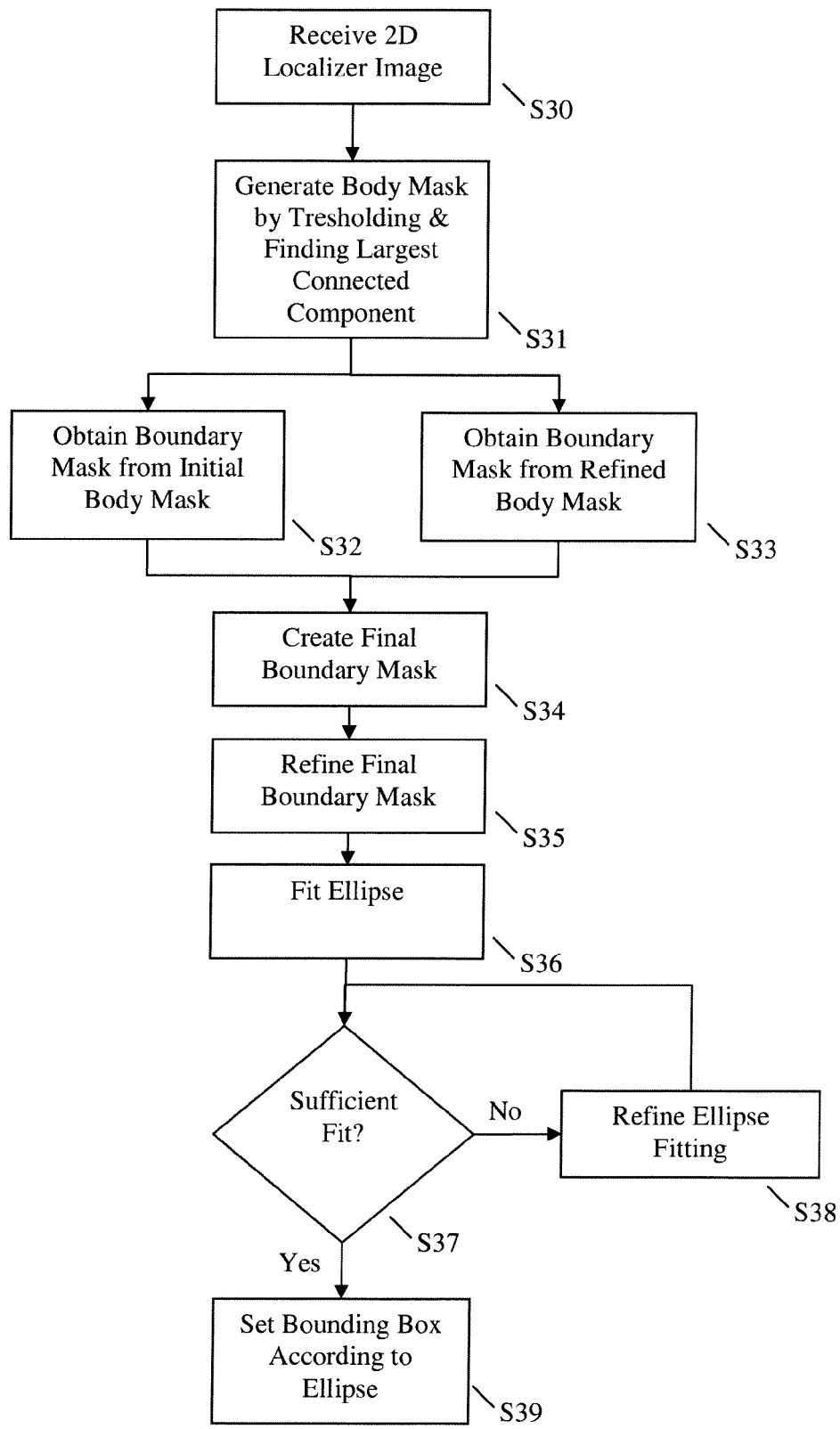
FIG. 3 is a flowchart illustrating a method for automatic FOV determination on a preprocessed localizer image according to an exemplary embodiment of the present invention.

Automatic FOV determination may be performed within the scope of the present invention by a variety of approaches. FIG. 3 is a flowchart illustrating a method for automatic FOV determination on a preprocessed localizer image according to an exemplary embodiment of the present invention. First, the preprocessed two-dimensional localizer images may be received (Step S30). It may be assumed, at this stage, that the received images are valid, for example, not blank; the initial FOV is sufficiently large; that there are no remaining shift artifacts; and that inhomogeneity correction has been performed. Exemplary embodiments of the present invention seek to locate the primary object within the image, which may be assumed to be the largest connected component present in a binary version of the localizer image that has been obtained by thresholding the localizer image in accordance with adaptive thresholding techniques known in the art. Accordingly, the localizer image may be converted into binary form by application of thresholding, a largest connected component may be identified within the binary image, and a body mask may be set as the largest connected component (Step S31).

In the process of converting the localizer image into a binary form, the intensity of each pixel may be thresholded to determine if the pixel is assigned a value of "1" indicating that the pixel includes tissue or a value of "0" indicating that the pixel represents empty space. There may then be multiple connected components within the binary image. For example, the patient's torso may appear as a first component, and a section of the patient's arm may appear as a second component that is not shown to connect to the patient's torso within the image. Other unrelated components may also be visible from the binary image. As it may be assumed that the largest connected component is the body of the patient, a body mask may be set to equal this largest connected component.

The body mask may indicate which pixels are considered part of the body and which pixels are considered not part of the body. As the body mask is set to the largest connected component, both empty space and minor components are excluded from the body mask.

From the body mask, one or more boundary masks may be generated. As the body mask indicates which pixels are part of the body, the boundary masks indicates which pixels belong to the perimeter of the body. According to an exemplary embodiment of the present invention, two boundary masks may be obtained. A boundary mask may be obtained for the initial body mask (Step S32) and a boundary mask may be obtained from a refined body mask (Step S33). The refined body mask may be a body mask that results from performing one or more processing effects on the initial body mask. This processing step may include, for example, a smoothing effect, a blurring effect, and/or a sharpening effect. Image processing may be performed on the body mask, for example, to compensate for noise or other irregularities that may be part of the body mask, for example, as a result of imperfect thresholding.

The two boundary masks may be obtained either concurrently or one after the other. There may even be more than two boundary masks obtained, for example, with each boundary mask being obtained using a different processing effect. Alternatively, exemplary embodiments of the present invention may be performed by obtaining only a single boundary mask. A final boundary mask may then be created from the one or more obtained boundary masks (Step S34), for example, by finding the intersection of the one or more masks. For example, the final boundary mask may be set as the outermost outline of all obtained boundary masks superimposed over each other.

The final boundary mask may then be refined by removing small isolated regions (Step S35). These small isolated regions may have been caused by noise, wrap-around artifacts or bodily extremities that were not previously removed during the generation of the body mask. Other refinement techniques may be applied in addition to or instead of the removal of the small isolated regions.

After the boundary mask has been refined, an ellipse may be fitted to the points of the refined final boundary mask (Step S36). The ellipse may be fitted, for example, using least squares approach or by some other means. After the ellipse has been fitted, it may be determined whether the fit is sufficient (Step S37). Sufficiency of the fitting may be tested, for example, by measuring the residual error that is calculated as the amount of the refined boundary mask that is not included in the ellipse and the amount of the ellipse that is not included in the refined boundary mask. If it is determined that the fitting is not sufficient (No, Step S37), then the ellipse fitting may be refined (Step S38). When it is determined that the ellipse fitting is sufficient (Yes, Step S37), then a bounding box representing a determined FOV may be set in accordance with the orientation of the ellipse (Step S39). In fitting the bounding box to the ellipse, the smallest rectangle that fully encloses the ellipse is selected. In so doing, the long axis of the ellipse may match the long axis of the bounding box and the short axis of the ellipse may match the short axis of the bounding box. Thus, the setting of the bounding box may include both the sizing and the orienting of the box around the ellipse. The resulting bounding box may then be used as the automatically determined FOV for the subsequent MRI study.

Figure 4:
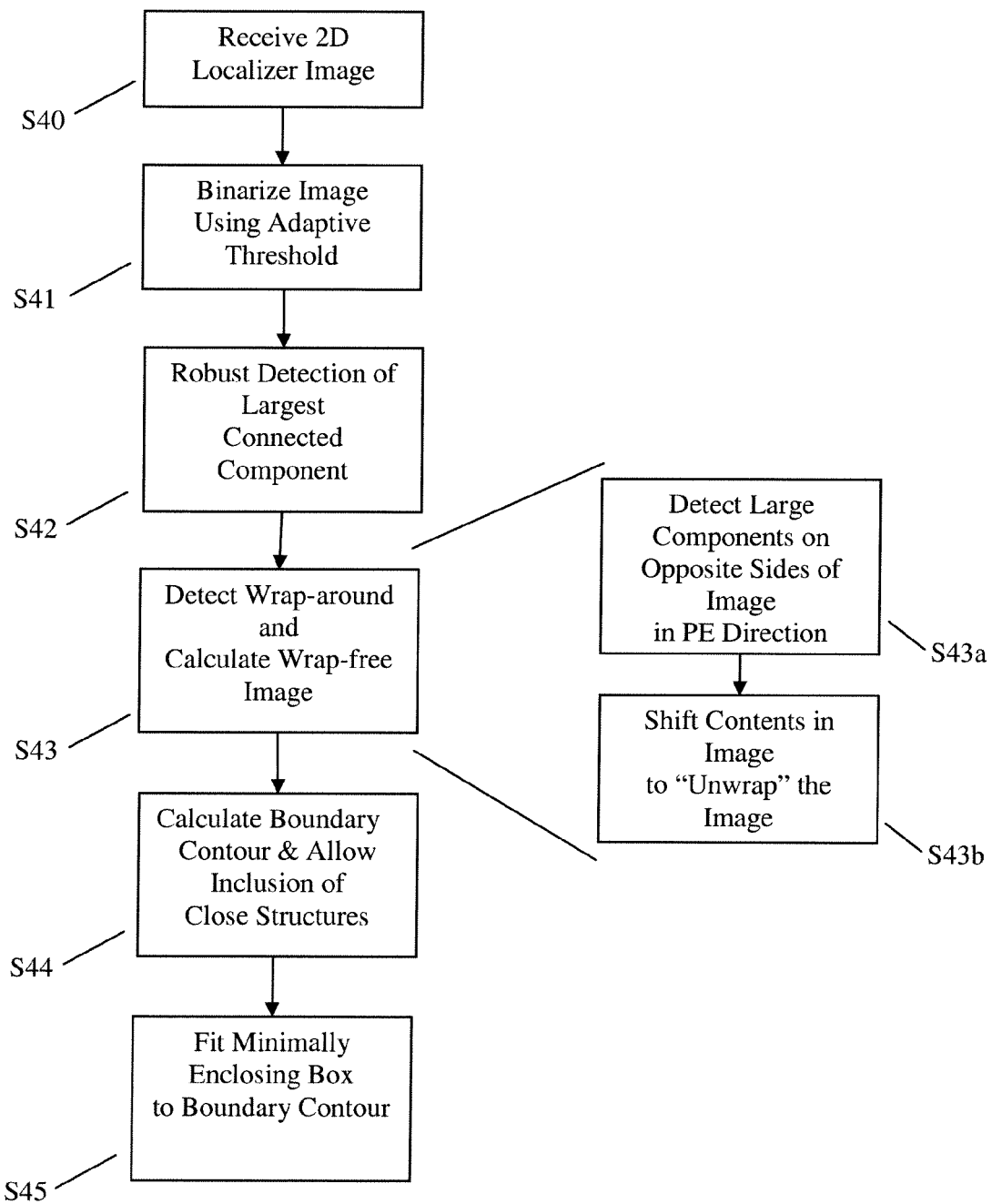
FIG. 4 is a flowchart illustrating a method for automatic FOV determination on a preprocessed localizer image according to an exemplary embodiment of the present invention.

Exemplary embodiments of the present invention may alternatively or additionally use a second approach for automatic FOV determination. FIG. 4 is a flowchart illustrating a method for automatic FOV determination on a preprocessed localizer image according to an exemplary embodiment of the present invention.

FIG. 4 is a flowchart illustrating a method for automatic FOV determination on a preprocessed localizer image according to an exemplary embodiment of the present invention. As discussed above with reference to FIG. 3, first, the preprocessed two-dimensional localizer images may be received (Step S40). It may be assumed, at this stage, that the received images are valid, for example, not blank; the initial FOV is sufficiently large; that there are no remaining shift artifacts; and that inhomogeneity correction has been performed. Exemplary embodiments of the present invention seek to locate the primary object within the image, which may be assumed to be the largest connected component present in a binary version of the localizer image that has been obtained by thresholding the localizer image in accordance with adaptive thresholding techniques known in the art. Accordingly, the localizer image may be converted into binary form by application of adaptive thresholding (Step S41). Then, a largest connected component may be identified within the binary image (Step S42). Next, wrap-around artifacts may be searched for and detected, where present and the portion of the image that is free of wrap-around artifacts may be calculated (Step S43).

One way to detect and resolve wrap-around artifacts (Step S43) according to an exemplary embodiment of the present invention is to first detect large components on opposite sides of the image in the direction of the PE candidate (Step S43a). Then, the image contents may be shifted to re-integrate the wrapped image (Step S43b).

Next, boundary contours may be calculated (Step S44). Here, the boundary contours may be calculated such that structures close to the largest connected component may be included within the boundary contour. Then, a smallest box that can fully enclose the boundary contour may be fit (Step S45). This box may then be used as the FOV.

This embodiment may differ from the embodiment described above with respect to FIG. 3 in that no ellipse need be fit prior to establishing the FOV. However, in other ways not mentioned, this embodiment may include elements of the embodiment described above with respect to FIG. 3.

Figure 5:
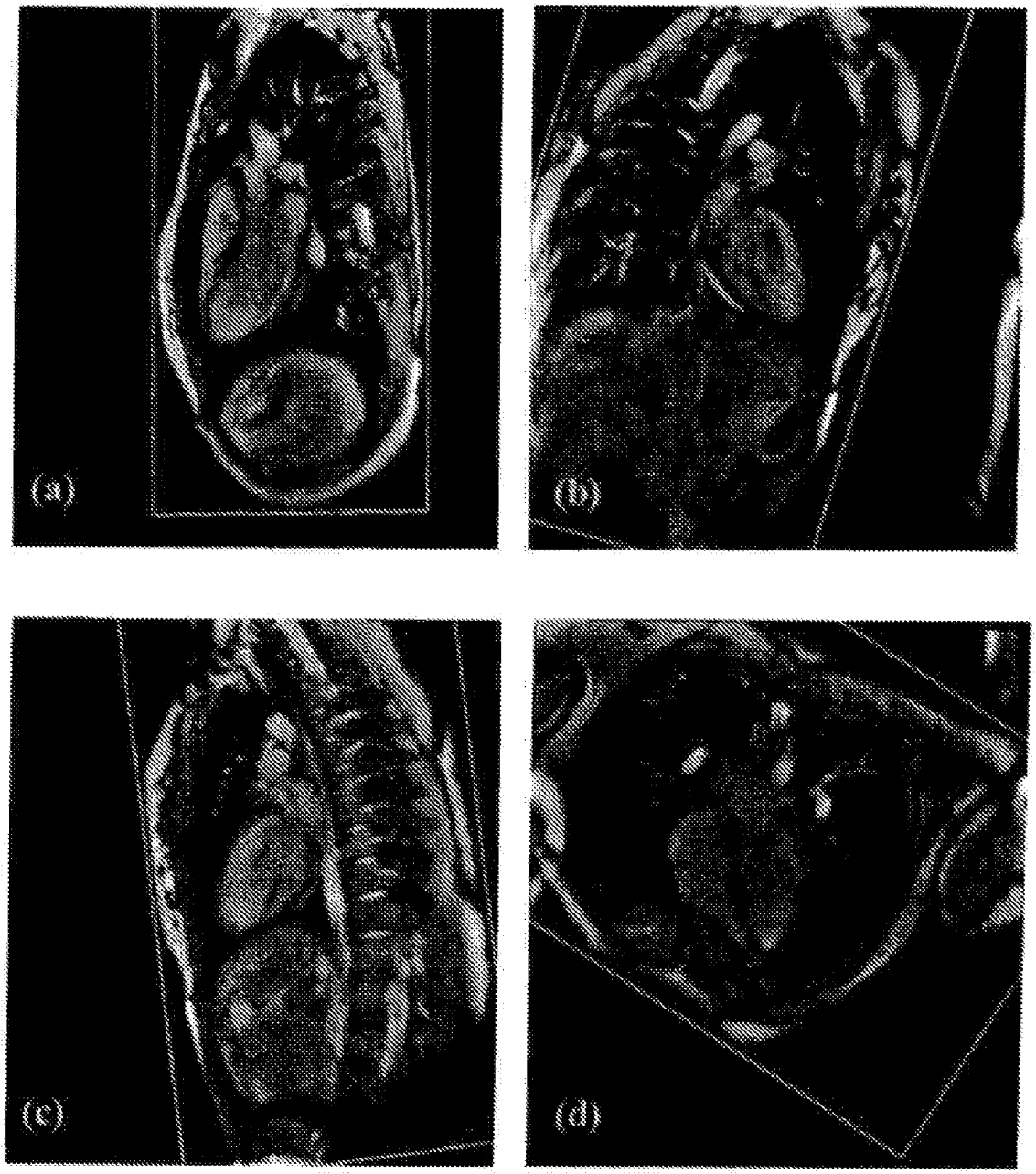
FIG. 5 is a set of four MR images (a), (b), (c), and (d) in which automatic determination of the FOV has been performed in accordance with exemplary embodiments of the present invention.
Figure 6:
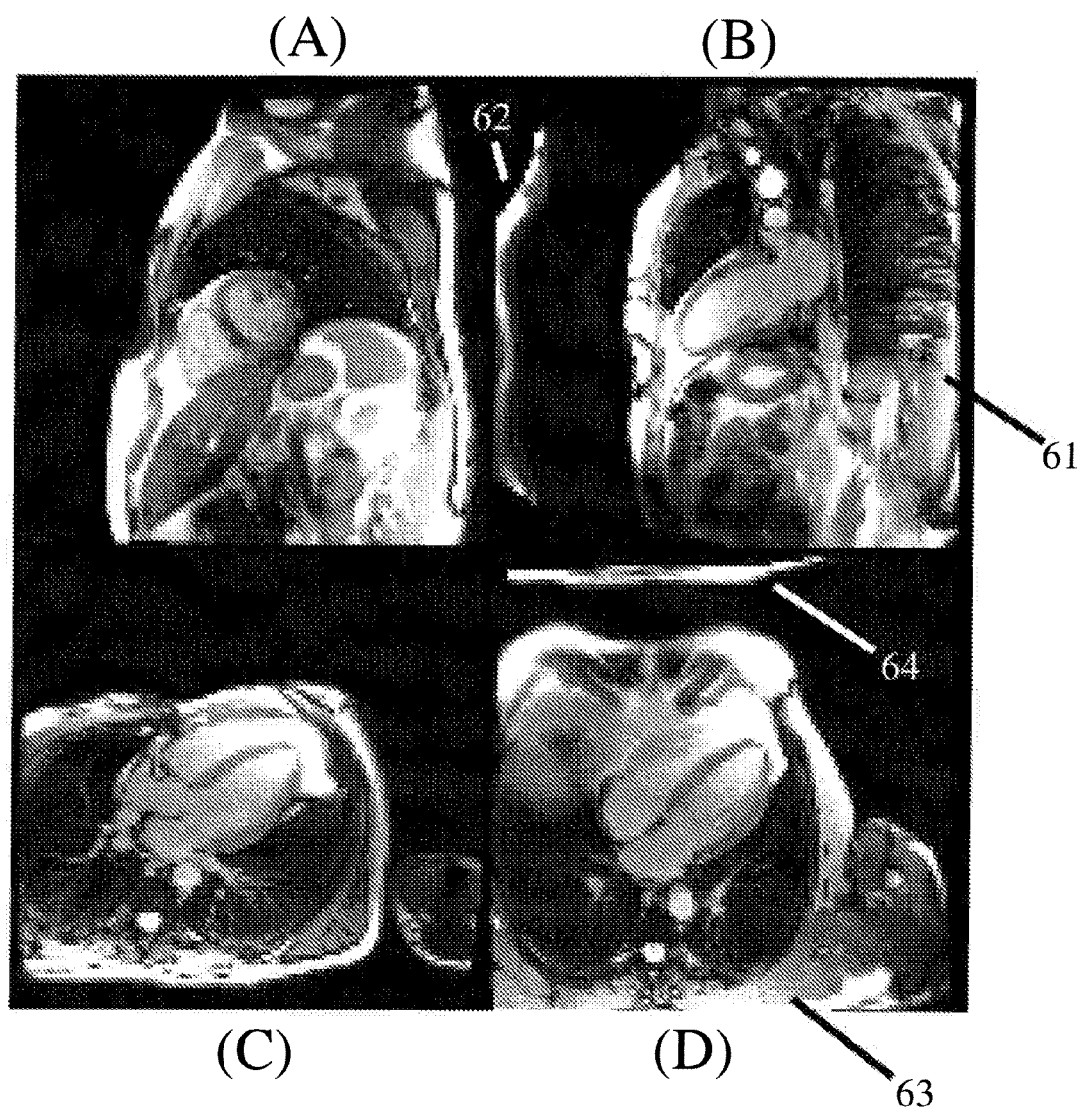
FIG. 6 is a set of four MR images (a), (b), (c), and (d) illustrating wrap-around artifacts.

FIG. 5 is a set of four MR images (a), (b), (c), and (d) in which automatic determination of the FOV has been performed in accordance with exemplary embodiments of the present invention. As can be seen from these images, the automatically determined FOV, shown as a white bounding box, surrounds the body mass, and as can be seen in FIG. 5(*b*), the arm is located outside of the FOV. In FIGS. 5(*b*) and (*c*), a two-chamber view of the heart can be seen. In FIG. 5(*d*), a four-chamber view of the heart can be seen. FIG. 5(*b*), shift artifacts have been successfully corrected.

Figure 7:
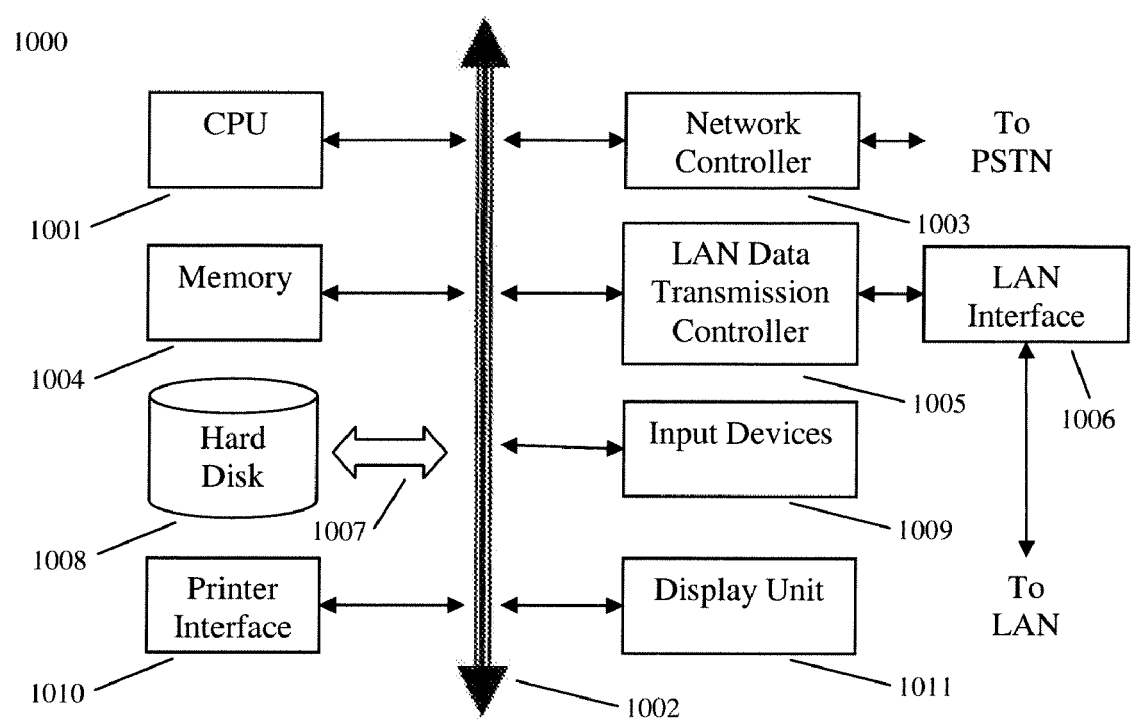
FIG. 7 shows an example of a computer system capable of implementing the method and apparatus according to embodiments of the present disclosure.

FIG. 7 shows an example of a computer system which may implement a method and system of the present disclosure. The system and method of the present disclosure 10 may be implemented in the form of a software application running on a computer system, for example, a mainframe, personal computer (PC), handheld computer, server, etc. The software application may be stored on a recording media locally accessible by the computer system and accessible via a hard wired or wireless connection to a network, for example, a local area network, or the Internet.

The computer system referred to generally as system 1000 may include, for example, a central processing unit (CPU) 1001, random access memory (RAM) 1004, a printer interface 1010, a display unit 1011, a local area network (LAN) data transmission controller 1005, a LAN interface 1006, a network controller 1003, an internal bus 1002, and one or more input devices 1009, for example, a keyboard, mouse etc. As shown, the system 1000 may be connected to a data storage device, for example, a hard disk, 1008 via a link 1007.

Exemplary embodiments described herein are illustrative, and many variations can be introduced without departing from the spirit of the disclosure or from the scope of the appended claims. For example, elements and/or features of different exemplary embodiments may be combined with each other and/or substituted for each other within the scope of this disclosure and appended claims.

What is claimed is:

1. A method for acquiring a medical imaging study using a medical imaging device, comprising:
   acquiring one or more preliminary images;
   generating a body mask by performing inhomogeneity correction, thresholding the preliminary images into a binary image, and identifying a largest connected component, wherein a connected component is defined as a contiguous set of pixels of the binary image having a value of one, wherein respective size of connected components is determined by area;
   defining a boundary mask as the boundary of the identified largest connected component of the generated body mask;
   fitting a rectangular bounding box to the defined boundary mask;
   setting the rectangular bounding box as a field of view for the medical imaging device; and
   performing a medical imaging study using the medical aging device set to use the rectangular bounding box as the field of view.

2. The method of claim 1, wherein the acquired preliminary images are preprocessed prior to the generation of the body mask.

3. The method of claim 2, wherein preprocessing the preliminary images includes:
   removing blank preliminary images;
   cropping regions without image data from the periphery of the preliminary images;
   establishing an initial field of view for each of the preliminary images;
   removing preliminary images where the initial field of view is not sufficiently large;
   correcting for shift artifacts caused by wrap-around in the preliminary images by transposing the shift artifacts to an opposite side of the initial field of view; and
   correcting for inhomogeneity.

4. The method of claim 1, wherein the one or more preliminary images are one or more two-dimensional localizer images of a lower diagnostic value than the medical imaging study.

5. The method of claim 1, wherein thresholding the preliminary images includes applying an adaptive thresholding technique to the preliminary images to characterize each image pixel as either a one, where the pixel intensity is above the adaptive threshold, or a zero, where the pixel intensity is below the adaptive threshold; and wherein the largest connected component is identified as the single region of the preliminary image that has the highest number of contiguous pixels with a value of one.

6. The method of claim 1, wherein obtaining the boundary mask includes:
   defining a first boundary mask as the boundary of the body mask;
   refining the body mask to establish a refined body mask;
   defining a second boundary mask as the boundary of the refined body mask; and
   creating the final boundary mask as the intersection of the first boundary mask and the second boundary mask, wherein the obtained boundary mask is the final boundary mask.

7. The method of claim 1, wherein fitting the rectangular bounding box to the obtained boundary mask includes:
   fitting an ellipse to the obtained boundary mask;
   refining the fitted ellipse; and
   setting the bounding box as the smallest possible rectangle that can enclose the fitted ellipse.

8. The method of claim 1, wherein the medical imaging device is an MRI.

9. The method of claim 1, further including detecting and correcting for shift artifacts caused by wrap-around in the one or more preliminary images after generating the body mask and prior to obtaining the boundary mask.

10. The method of claim 1, wherein the boundary mask includes not only the largest connected component of the body mask but also structures proximate to the largest connected component.

11. A computer system comprising:
    a processor; and
    a program storage device, embodying a program of instructions executable by the processor to perform method steps for automatically determining a field of view for performing a subsequent medical imaging study, the method comprising:
    acquiring one or more two-dimensional localizer images;
    preprocessing the localizer images;
    generating a body mask by performing inhomogeneity correction, thresholding the preprocessed localizer images into a binary image, and identifying a largest connected component, wherein a connected component is defined as a contiguous set of pixels of the binary image having a value of one, wherein respective size of connected components is determined by area;

defining a boundary mask as the boundary of the identified largest connected component of the generated body mask;

fitting a rectangular bounding box to the defined boundary mask; and using the rectangular bounding box as a field of view for performing a three-dimensional subsequent medical imaging study.

12. The computer system of claim 11, wherein preprocessing the localizer images includes:

removing blank localizer images;

cropping regions without image data from the periphery of the localizer images;

establishing an initial field of view for each of the localizer images;

removing localizer images where the initial field of view is not sufficiently large;

correcting for shift artifacts caused by wrap-around in the preliminary images by transposing the shift artifacts to an opposite side of the initial field of view; and correcting for inhomogeneity.

13. The computer system of claim 11, wherein thresholding the localizer images includes applying an adaptive thresholding technique to the localizer images to characterize each image pixel as either a one, where the pixel intensity is above the adaptive threshold, or a zero, where the pixel intensity is below the adaptive threshold; and wherein the largest connected component is identified as the single region of the localizer image that has the highest number of contiguous pixels with a value of one.

14. The computer system of claim 11, wherein obtaining the boundary mask includes:

defining a first boundary mask as the boundary of the body mask;

refining the body mask to establish a refined body mask;

defining a second boundary mask as the boundary of the refined body mask; and creating the final boundary mask as the intersection of the first boundary mask and the second boundary mask, wherein the obtained boundary mask is the final boundary mask.

15. The computer system of claim 11, further including detecting and correcting for shift artifacts caused by wrap-around in the one or more localizer images after generating the body mask and prior to obtaining the boundary mask.

* * * * *